US012583971B2

(12) United States Patent
Dolatkhani et al.

(10) Patent No.: US 12,583,971 B2
(45) Date of Patent: Mar. 24, 2026

(54) BIOSOURCED GELLING POLYAMIDES

(71) Applicant: POLYMEREXPERT SA, Pessac (FR)

(72) Inventors: Marc Dolatkhani, Cestas (FR); Eric Lutz, Pessac (FR); Marie Odile Hecht, Pessac (FR); Olga Siscan, Pessac (FR); Victor Salvado, Merignac (FR); Anne Pagnoux, Le Barp (FR)

(73) Assignee: POLYMEREXPERT SA, Pessac (FR)

( * ) Notice: Subject to any disclaimer, the term of this patent is extended or adjusted under 35 U.S.C. 154(b) by 1011 days.

(21) Appl. No.: 17/754,886

(22) PCT Filed: Oct. 15, 2020

(86) PCT No.: PCT/FR2020/051849

§ 371 (c)(1),
(2) Date: Apr. 14, 2022

(87) PCT Pub. No.: WO2021/074541

PCT Pub. Date: Apr. 22, 2021

(65) Prior Publication Data

US 2024/0124650 A1 Apr. 18, 2024

(30) Foreign Application Priority Data

Oct. 16, 2019 (FR) ....................................... 1911530

(51) Int. Cl.

| | |
|---|---|
| ***C08G 69/44*** | (2006.01) |
| ***A61K 8/04*** | (2006.01) |
| ***A61K 8/88*** | (2006.01) |
| ***A61K 8/92*** | (2006.01) |

(52) U.S. Cl.
CPC .............. *C08G 69/44* (2013.01); *A61K 8/042* (2013.01); *A61K 8/88* (2013.01); *A61K 8/92* (2013.01)

(58) Field of Classification Search
CPC .......... C08G 69/44; A61K 8/042; A61K 8/88; A61K 8/92
See application file for complete search history.

(56) References Cited

U.S. PATENT DOCUMENTS

| | | | | |
|---|---|---|---|---|
| 5,703,177 | A | 12/1997 | Hoff | |
| 6,111,055 | A | 8/2000 | Berger et al. | |
| 2010/0093971 | A1* | 4/2010 | Harris .................... | C08G 69/44 528/292 |

FOREIGN PATENT DOCUMENTS

| | | | |
|---|---|---|---|
| JP | S62135521 | A | 6/1987 |
| WO | 9817705 | A1 | 4/1998 |
| WO | 2014044809 | A1 | 3/2014 |

OTHER PUBLICATIONS

Database WPI, Thomson Scientific, 1987, vol. 1987, No. 30, XP002799536 , pp. 1-3.
International Search Report for Corresponding International Application No. PCT/FR2020/051849, Dec. 11, 2020, 2 pages.

* cited by examiner

*Primary Examiner* — Alma Pipic
(74) *Attorney, Agent, or Firm* — LUCAS & MERCANTI, LLP

(57) ABSTRACT

The invention relates to novel biosourced polyamide derivatives able to form gels, the method for preparing same, the gels formed from these gelling polyamides, as well the compositions containing them, in particular cosmetic compositions.

20 Claims, No Drawings

BIOSOURCED GELLING POLYAMIDES

CROSS-REFERENCE TO RELATED APPLICATIONS

This application is a 371 of PCT/FR2020/051849, filed Oct. 15, 2020, which claims the benefit of French Patent Application No. 1911530, filed Oct. 16, 2019.

FIELD OF THE INVENTION

The invention relates to novel gelling polyamide derivatives of biosourced origin, the method for preparing same and the production of novel gels in organic media (oils) from them. The invention also relates to the gels formed from these gelling polyamides, as well as the compositions containing them, in particular cosmetic and pharmaceutical compositions.

SUMMARY OF THE INVENTION

The method according to the invention makes it possible to obtain a polyamide compound able to form gels having the properties sought, by implementing two manufacturing steps. In a first step, an amide derivative of low molar mass is first obtained by functionalizing a diacid by a diamine, conferring the gelling properties of the compound of the invention, the diacid and the diamine being able to be biosourced. This step is followed by adding a diacid polyester to the polyamide compound obtained initially, in order to obtain a polyamide compound soluble in the oils and able to gel them.

Another object of the invention is the gels obtained from these gelling polyamides. These gels are characterized by the texture thereof that is pleasant to touch, the transparency thereof, the low gelling-polyamide content thereof, the ability thereof to disperse at temperatures below 85° C., the thermoreversible and rheofluidizing character thereof and the possibility of being 100% composed of products of natural origin.

BACKGROUND OF THE INVENTION

In the case of the gelling of cosmetic oils, the gelling polyamide must meet various precise criteria. For cost reasons, in the use thereof in a cosmetic product, the gelling polyamide must first of all be capable of gelling the organic phase at a low concentration, i.e., preferably, below 10% by weight. In addition, an important aspect for a cosmetic application is the feel of the product. This is because incorporating the gelling agent must not cause an excessively marked granular effect on the cosmetic product.

It is therefore sought to have available gelling compounds that possess these properties.

The application WO 98/17705 describes the preparation of polyamides with ester terminations capable of gelling oils, by a method in one step. The synthesized polyamides are capable of gelling tetradecane. However, the polyamides obtained are not biosourced in character and therefore do not have the natural origin desired for the present invention. In addition, the polymers obtained can gel only a small number of oils, and require the use of high concentrations for obtaining strong gels, which gives rise to high manufacturing costs for a cosmetic formulation.

It is therefore sought to find alternatives making it possible to gel oils that are most frequently used, such as caprylic/capric triglyceride, or plant oils, with lower concentrations.

DETAILED DESCRIPTION OF THE INVENTION

It has now been found that novel polyamide derivatives, prepared from polyester of natural origin, were particularly adapted for gelling plant and organic oils, and made it possible to obtain a gel having the qualities sought, in particular for a cosmetic and/or pharmaceutical application.

It has also been found that the polyamides according to the invention exhibited ease of use in cosmetic formulations and made it possible to confer thereon a smooth texture.

"Natural origin" means a product partially or entirely prepared from natural materials (animal or plant) chemically modified or not. Such a product can also be termed "biosourced" or "of biosourced origin", these terms being normally used in the polymer field.

Biosourced products or of biosourced origin generally come from vegetable matter such as trees or plants, for example sugar cane, beetroot, sunflower, palm, ricin and others, or from animal matter such as fats.

The proportion of content of natural origin of the polyamide, expressed as a percentage by weight, can be calculated, in particular, in accordance with the NF ISO 16128-2 standard.

Diacids of natural and/or biosourced origin can, for example, be selected from:

- 2,5-furandicarboxylic acid ($C_6H_5O_4$), obtained by biofermentation of fructose for example;
- itaconic acid ($C_5H_6O_4$), obtained from fructose for example;
- succinic acid ($C_4H_6O_4$), obtained from glucose fermented by E.coli for example;
- glutaric acid ($C_5H_8O_4$), obtained from sugar for example;
- adipic acid ($C_6H_{10}O_4$), obtained from saccharic acid for example;
- heptanedioic acid ($C_7H_{12}O_4$), obtained from castor oil for example;
- azelaic acid ($C_9H_{16}O_4$), obtained from oleic acid for example;
- sebacic acid ($C_{10}H_{18}O_4$), obtained from castor oil for example;
- undecanedioic acid ($C_{11}H_{20}O_4$), obtained from castor oil for example;
- dodecanedioic acid ($C_{12}H_{22}O_4$), obtained from biofermenting lauric acid (coconut) for example;
- brassylic acid ($C_{13}H_{24}O_4$), obtained from erucic acid (colza) for example;
- tetradecanedioic acid ($C_{14}H_{26}O_4$), obtained by biofermenting myristic acid (coconut) for example;
- hexadecanedioic acid ($C_{16}H_{30}O_4$), obtained by biofermenting palmitic acid (palm) for example;
- octadecanedioic acid ($C_{18}H_{34}O_4$), obtained by biofermenting stearic acid for example;
- eicosanedioic acid ($C_{20}H_{38}O_4$), obtained by biofermenting arachidic acid (colza) for example;
- docosanedioic acid ($C_{20}H_{38}O_4$), obtained by metathesis of undecylenic acid (castor) for example;
- fatty-acid dimers (including 36 carbon atoms in particular), obtained from unsaturated acids, such as for example oleic acid;
- diacid polyesters (polyester including chain-end acid functions), obtained from biosourced-oil derivatives.

Amines of natural origin and/or biosourced can in particular be obtained by amination of the previously mentioned dicarboxylic acids, for example:

- butanediamine ($C_4H_{12}N_2$), obtained by amination of succinic acid;

hexamethylene diamine ($C_6H_{16}N_2$), obtained by amination of adipic acid;

fatty diamine dimers (including 36 carbon atoms in particular), obtained by amination of fatty acid dimers.

Advantageously, the novel polyamide derivatives according to the invention can be prepared by a synthesis method comprising a step of forming a precursor, and a step of adding a diacid polyester, providing the final compound with solubility in oils.

The invention therefore relates to the polyamide compounds of formula (1)

(1)

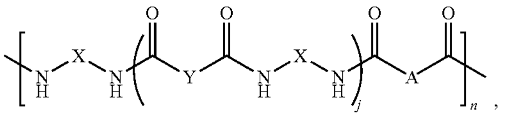

wherein:

A =

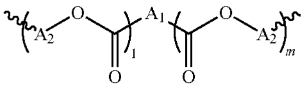

$A_1$ represents an alkyl radical, linear or branched, comprising from 2 to 40 carbon atoms, preferably from 2 to 12, and in particular from 2 to 6, said radical optionally comprising one or more unsaturations, being optionally interrupted by at least one heteroatom selected from O, N and S, and being optionally substituted by at least one —OAlk substituent, Alk representing an alkyl group comprising from 1 to 10 carbon atoms;

$A_2$ represents an alkyl radical, linear or branched, comprising from 2 to 30 carbon atoms, preferably from 5 to 22, in particular 5 to 18, said radical optionally comprising one or more unsaturations, and being optionally substituted by at least one —OAlk substituent, Alk representing an alkyl group comprising from 1 to 10 carbon atoms;

l and m represent, independently of each other, an integer from 1 to 20, preferably from 1 to 10, the sum l+m preferably being from 2 to 20;

n is an integer from 1 to 20, preferably from 1 to 8;

j is an integer from 1 to 10, preferably from 1 to 3;

X represents an alkyl radical, linear or branched, comprising from 2 to 60 carbon atoms, preferably 16 to 45 carbon atoms, said radical optionally comprising one or more unsaturations;

Y represents an alkyl radical, linear or branched, comprising from 3 to 35 carbon atoms, preferably from 6 to 18 carbon atoms, said radical optionally comprising one or more unsaturations, or a heterocycle having 3 to 10 members and comprising 1 or 2 heteroatoms selected from O, N and S.

Preferably, $A_1$ represents a linear alkyl radical comprising from 2 to 12, preferably from 2 to 6, in particular 3 carbon atoms, said radical optionally comprising one or more unsaturations.

Preferably, $A_2$ represents an alkyl radical, linear or branched, comprising from 5 to 18 carbon atoms, said radical optionally comprising one or more unsaturations, and preferentially a group of formula

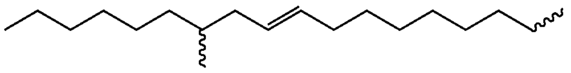

Advantageously, the sum l+m has a mean value of 7, 11 or 15.

In the above formulae A and $A_2$, the sign  represents a bond of the segment in question with the main chain.

Preferred polyamide compounds of formula (1) are those wherein:

$A_1$ represents a linear alkyl radical comprising 3 carbon atoms;

$A_2$ represents a branched alkyl radical comprising 17 carbon atoms;

l and m represent, independently of each other, an integer from 3 to 4, the sum l+m preferably being from 6 to 8;

n is an integer from 1 to 8, preferably from 1 to 3;

j is an integer from 1 to 10, preferably from 1 to 3;

X represents a branched alkyl radical comprising 36 carbon atoms;

Y represents a linear alkyl radical comprising 8 carbon atoms.

In the present description, unless stipulated to the contrary, the value ranges indicated include the bounds.

The invention also relates to a method for preparing gelling polyamides. The objective of preparing the gelling polyamide is to chemically modify a polyester, soluble in oils, in particular vegetable oils, in order to incorporate therein amide groups thus providing the required gelling properties.

According to the invention, said method for preparing gelling polyamides of formula (1)

(1)

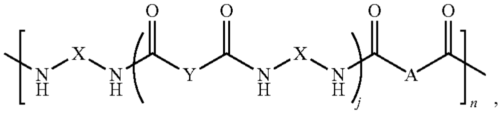

comprises the following steps:

1) Preparing a diamine polyamide by functionalizing a diacid of formula (2) by a diamine of formula (3) to obtain a diamine polyamide of formula (4):

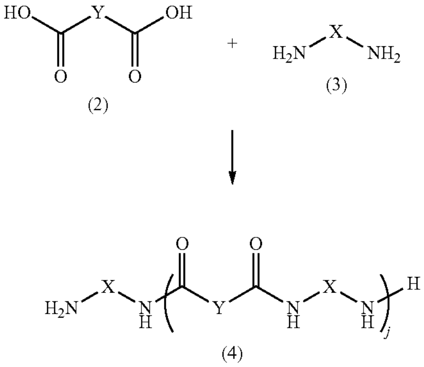

wherein:

X represents an alkyl radical, linear or branched, comprising from 2 to 60 carbon atoms, preferably 16 to 45 carbon atoms, said radical optionally comprising one or more unsaturations;

Y represents an alkyl radical, linear or branched, comprising from 3 to 35 carbon atoms, preferably 6 to 18 carbon atoms, said radical optionally comprising one or more unsaturations or a heterocycle having 3 to 10 members and comprising 1 or 2 heteroatoms selected from O, N and S j is an integer from 1 to 10, preferably from 1 to 3;

2) Modifying a diacid polyester of formula (5)

(5)

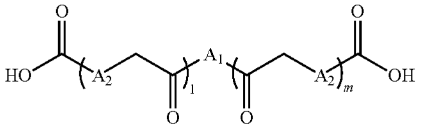

by adding the diamine polyamide of formula (4)

(4)

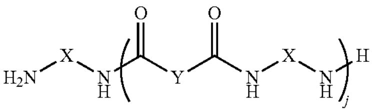

leading to the polyamide of formula (1) having gelling properties, wherein:

A =

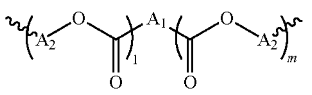

$A_1$ represents an alkyl radical, linear or branched, comprising from 2 to 40 carbon atoms, preferably from 2 to 12, and in particular from 2 to 6, said radical optionally comprising one or more unsaturations, optionally being interrupted by at least one heteroatom selected from O, N and S, and optionally being substituted by at least one —OAlk substituent, Alk representing an alkyl group comprising from 1 to 10 carbon atoms;

$A_2$ represents an alkyl radical, linear or branched, comprising from 2 to 30 carbon atoms, preferably from 5 to 22, said radical optionally comprising one or more unsaturations, and optionally being substituted by at least one —OAlk substituent, Alk representing an alkyl group comprising from 1 to 10 carbon atoms;

l and m represent, independently of each other, an integer from 1 to 20, preferably from 1 to 10, the sum l+m preferably being from 2 to 20;

n is an integer from 1 to 20, preferably from 1 to 8;

X, Y, j are as defined previously.

The diamine polyamide of formula (4) is, in the description, indifferently named "diamine precursor" or "diamine functionalized precursor".

Optionally, the method according to the invention may furthermore comprise an additional step comprising terminating the chains of the polyamide compound of formula (1) by adding an alcohol termination compound of formula (6), leading to a polyamide compound of formula (7):

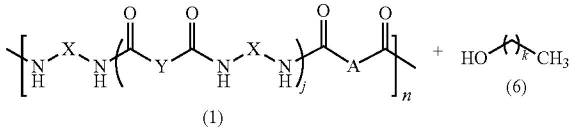

(1) (6) (7)

wherein:

A =

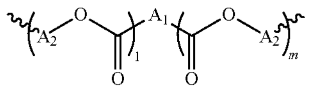

X, Y, A, $A_1$, $A_2$, j, n are as defined previously;

k is an integer from 2 to 60, preferably from 8 to 40.

Advantageously, the polyamide compound of formula (7) has improved solubility in vegetable oils.

The polyamide compound of formula (7) and use thereof as gelling agent also represent aspects of the invention.

(7)

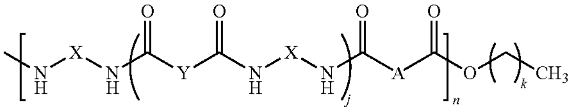

All the preferred aspects relating to A, $A_1$, $A_2$, X, Y, I, m, n, k and j mentioned above for the polyamide compounds of formula (1) also apply to the polyamide compounds of formula (7) and to the preparation method according to the invention.

The diacid polyester of formula (5)

(5)

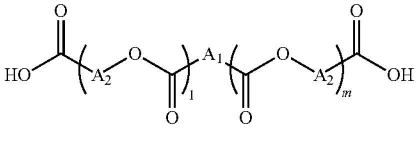

wherein $A_1$, $A_2$, l and m are as defined above, is commercially available under the name PRICA® (ITERG), or can be prepared by condensing a diacid of formula (8) with a hydroxylated ester derivative or hydroxylated fatty acid of formula (9) according to a protocol derived from the application WO 2014/044809:

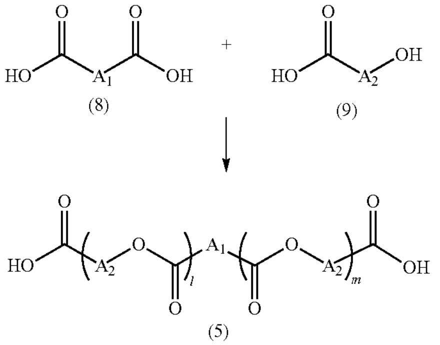

(8) (9)

(5)

The $1^{st}$ step of the method for preparing a gelling polyamide compound (1), namely the step of forming a diamine precursor (4) by functionalizing a diacid (2) by a diamine (3), allows manufacture of the gelling block. This step preferably has a duration of between 1 h and 24 h, preferably between 4 h and 16 h. The reaction is preferably implemented at a temperature of between 100° C. and 240° C., in particular between 130° C. and 160° C. This step is preferably implemented in a sealed system previously dried and put under vacuum.

The $1^{st}$ step is preferably implemented by mixing a diacid equivalent (2) and a quantity of diamine (3) of between 1 and 4 equivalents. The quantity of diamine equivalents (3) used can be calculated for example according to the amine value thereof.

Generally, the equivalents are calculated according to the levels of acid and amine supplied by manufacturers of raw materials in the CoA (Certificate of Analysis) of the product or are determined by quantitative analysis.

The diacid of formula (2) can be selected, for example, from the $C_4$-$C_{12}$ aliphatic diacids, such as sebacic acid, adipic acid or succinic acid or the diacids comprising a heterocycle having 3 to 10 members and comprising 1 or 2 heteroatoms selected from O, N and S, such as furandicarboxylic acid (FDCA).

The diamine of formula (3) may comprise, for example, an alkyl radical comprising 30 to 40 carbon atoms.

A preferred diacid of formula (2) is sebacic acid and a preferred diamine of formula (3) is a dimer diamine including on average 36 carbon atoms, sold by Croda under the name Priamine®.

The $2^{nd}$ step of the method according to the invention (modification of the polyester polyamide) preferably has a duration of between 30 min and 24 h, in particular between 2 h and 10 h. The reaction can be implemented, for example, at a temperature of between 100° C. and 240° C., preferably between 130° C. and 160° C., by adding diacid polyester in a reactor containing the precursor formed during step 1, previously heated and stirred at the temperature of step 2.

The ratio between the diacid polyester (5) and the diamine precursor (4) is one of the factors that influences the gelling capabilities of the end product.

The ratio between the diamine precursor (4) and the diacid (5) is selected so that the compound (1) no longer has any chain-end amine functions, but only carboxylic acid or alcohol functions.

A quantity of diamine precursor (4) of between 0.2 and 1 equivalent (eq), and more particularly between 0.4 and 0.7 equivalents (eq) will preferably be used for 1 equivalent of diacid polyester (5).

Advantageous, the $2^{nd}$ step is implemented by adding 1 equivalent of diacid polyester (5) to a quantity of diamine precursor (4) of between 0.2 and 1 equivalent, at a temperature of between 100 and 240° C., preferably between 130 and 150° C.

At the end of the $2^{nd}$ step, the gelling polyamide is formed, and the gelling polyamide can be recovered, for example, by pouring it at a temperature above 100° C. from the reactor to an adapted receptacle.

The method according to the invention has the advantage of consisting of a mass polymerization, using biosourced compounds and/or ones of natural origin. The gelling polyamides thus obtained make it possible to obtain gels that can be 100% biosourced when the gelling polyamide is solubilized in a vegetable oil.

In addition, implementing the synthesis in two steps allows the manufacture of small polyamide blocks providing the gelling properties, and then the grafting of these groups on polyesters that then provide the properties of solubility of the compound in the oils of vegetable origin.

The invention also relates to the use of the gelling polyamide according to the invention, or obtained according to the method of the invention, as a gelling agent for organic media, in particular vegetable oils. In particular, the invention also relates to the use of the gelling polyamide according to the invention, or obtained according to the method of the invention, as gelling agent of oils selected for example from vegetable oils or oils of natural origin, such as caprylic/capric triglyceride, helianthus annuus seed oil, ethylhexyl palmitate, castor oil, coconut oil, glycine soya oil, polyglyceryl-4 oleate (and) glyceryl olivate (and) hydrogenated rapeseed alcohol, isopropyl myristate, dicaprylyl carbonate, ethyl oleate, prunus domestica seed oil, prunus amygdalus dulcis oil, sesamum indicum seed oil, simmondsia chinensis seed oil, olea europaea fruit oil, vitis vinifera seed oil, punica granatum seed oil, ricinus communis seed oil, triticum vulgare germ oil, octyldodecanol, coco-caprylate, and corylus avellana seed oil (INCI name).

The gelling polyamide according to the invention can also form a clear transparent gel with the non-polar oils if they are mixed with more polar oils, such as for example a mixture containing 70% C15-19 alkane or 70% squalane with 30% caprylic/capric triglyceride.

Advantageously, the gelling polyamide of formula (1) or (7), as described above, makes it possible to obtain a gel having a combination of advantageous properties, namely: gel strength properties, transparency properties, a texture that is pleasant to the touch and fillers uniformly distributed in the gel by virtue of the suspension capability of said polyamide with respect to said fillers in the gel, these properties in addition being obtained using a biosourced compound.

"Suspension capability" means the ability to maintain solids in suspension in the medium without precipitation occurring.

Advantageously, the gel obtained from the gelling polyamide of formula (1) or (7), as described above, is rheofluidizing (its dynamic viscosity decreases when the shear rate increases) and thixotropic (its apparent viscosity decreases when it is subjected to a constant shear rate, and returns to its initial value when the shearing is stopped).

The gelling polyamide according to the invention can also be used for forming beads of gelled oil in suspension in an aqueous medium. For this purpose, the gelling polyamide will be previously dispersed in an oil of interest, and then beads will be obtained by adding gelled oil in the aqueous phase, either by mechanical dispersion, or by microfluidic methods (millimetric beads). The mixture can optionally be stabilized either by adding surfactants to obtain a suspension, or by adding coacervation agents. The advantages provided by the gelling agent consist of increased mechanical properties of the beads, as well as a pleasant texture and greater stability of the beads in suspension in the aqueous phase.

The invention also relates to a method for gelling at least one oil selected, for example, from vegetable oils and mixtures of non-polar oils and more polar oils, in particular of natural origin, wherein a gelling polyamide of formula (1) or (7) as described above, according to the invention, or obtained by the preparation method described above, is added to said oil or oils, or to a composition containing it or them.

The invention also relates to the gels containing or formed from said gelling polyamides.

In particular, the gels comprising the gelling polyamide according to the invention, or obtained according to the method of the invention, and at least one oil acceptable on a pharmaceutical or cosmetic level are an object of the invention.

According to a preferred aspect, the gelling polyamide according to the invention, or obtained according to the method of the invention, makes it possible to form, for example, a rheofluidizing and thixotropic gel in a proportion of 5% by weight in the caprylic/capric triglyceride.

The gelling polyamide according to the invention, or obtained according to the method of the invention, as gelling agent forms gels in caprylic/capric triglyceride, the viscosity of which increases with the concentration of said gelling agent.

The gel formed with the gelling polyamide according to the invention, or obtained according to the method of the invention, can in particular reach an optimum viscosity only 4 hours after preparation thereof, and remain the same 48 h later.

The gelling polyamides according to the invention make it possible to form viscous gels containing up to 5% ethanol.

Equally, the gelling polyamide according to the invention, or obtained according to the method of the invention, makes it possible to gel oils and to stabilize mixtures containing up to 4% waxes with the following waxes: beeswax, C10-18 triglycerides, behenyl alcohol, glyceryl stearate, synthetic wax, pentaerythrityl distearate, copernica cerifera wax, cetearyl alcohol, cetyl alcohol, rice bran wax, sunflower wax, hydrogenated cocoglycerides, glyceryl dibehenate, C18-36 acid triglyceride. (INCI name).

The gelling polyamide also makes it possible to gel oils and to stabilize mixtures containing up to 4% by weight butters with, for example, the following butters: shea butter, apricot butter, coconut butter.

The invention also relates to the gels containing or formed from the gelling polyamide according to the invention, or obtained according to the method of the invention. The gelling polyamides of formula (1) or (7) make it possible to easily prepare completely natural oily clear gels.

The gelling polyamides according to the invention also make it possible to form clear gels with the sunscreens such as ethylhexyl methoxycinnamate, ethylhexyl salicylate, homosalate, octocrylene.

The proportion by weight of the gelling polyamide in said gel is preferably from 0.5 to 10%, in particular from 3 to 8%.

Another object of the invention is the compositions comprising a gelling polyamide of formula (1) or (7) as described above or obtained according to the method of the invention, or comprising the gels containing or formed from said gelling polyamides, in particular the pharmaceutical or cosmetic compositions.

Said pharmaceutical or cosmetic compositions may comprise active ingredients and vehicles and additives that are pharmaceutically acceptable or acceptable in cosmetics.

The proportion by weight of the gelling polyamide in a cosmetic composition according to the invention may for example be between 0.5% and 10%, preferably from 1 to 10%, in particular from 3 to 8%. The gelling polyamides according to the invention, or obtained according to the method of the invention, can therefore be associated in cosmetics with polar, non-polar or vegetable oils, or perfumes.

They are in particular compatible with organic and mineral sunscreens, pigments and nacres, the oily additives normally used in cosmetics, cosmetic butters and waxes, or emulsifiers.

The gelling polyamide also makes it possible to gel oils and to stabilize mixtures containing up to 10% surfactant, for example: PEG-20 sorbitan oleate, PEG-20 glyceryl triisostearate, polyglyceryl-4 oleate, polyglyceryl-4 stearate.

The gelling polyamide also makes it possible to gel oils and to stabilize mixtures containing up to 5% suspension agent such as silica, titanium dioxide, clay, mica, Luffa cylindrica fruit, cellulose acetate and vaccinium microcarpon fruit powder.

The gelling polyamides described above can be incorporated in various anhydrous galenic formulations such as anhydrous gel, sprayable gel, pumpable gel, nacreous gel, colored gel, lip salve, lipstick, exfoliating gel, perfumed gel, sun jelly, oily makeup-removal gel, etc.

They can also be incorporated in formulations of the emulsion type, such as for example a water in oil emulsion, an oil in water emulsion, a sun emulsion, a water in oil foundation, an oil in water foundation, etc.

The gelling polyamide according to the invention, or obtained according to the method of the invention, is particularly adapted for use in a cosmetic composition.

The invention is illustrated by the following examples.

In the examples, the diacid polyester PRICA 2405® is a polyester sold by ITERG, the Institut des Corps Gras. Priamine 1075® is a diamine sold by Croda. Sebacic acid comes from Arkema (biosourced) or from Sigma Aldrich. Labrafac CC® (INCI name: caprylic/capric triglyceride, also hereinafter referred to as "CCT") comes from Gattefossé. Sunflower oil (INCI name: helianthus annuus seed oil) comes from IES Labo.

Preparations 1 to 9 describe synthesizing the diamine functionalized precursor of formula (4), which constitutes the gelling block of the end product.

Examples 1 to 9 and 11 to 13 relate to the gelling polyamide compounds of formula (1). Example 10 is a comparative example. Example 14 describes the preparation of a gelling polyamide compound of formula (7).

Examples 15 to 23 relate to the study of the properties of the gelling polyamide compounds of formula (1) and the compositions containing same.

EXAMPLES

Preparation 1: Preparation of the diamine functionalized precursor (4) from 1 equivalent of diacid (2) for 2 equivalents of diamine (3).

The diamine functionalized precursor is prepared from sebacic acid and Priamine 1075®.

32.01 g of Priamine 1075® and 6.00 g of sebacic acid are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 600 g/mol.

Preparation 2: Preparation of the diamine functionalized precursor (4) from 1 equivalent of diacid (2) for 2.5 equivalents of diamine (3).

The diamine functionalized precursor is prepared from sebacic acid and Priamine 1075®.

40.07 g of Priamine 1075® and 6.00 g of sebacic acid are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 590 g/mol.

A gelling test was implemented. The gel is produced at a concentration of 5% by weight of the product obtained in CCT (caprylic/capric triglyceride). 0.5 g of the end product are introduced and supplemented with 9.51 g of CCT in a 20 mL pill container. The crimped pill container is placed in a horizontal stirrer preheated to 100° C. and stirred for 30 min. After 24 h at ambient temperature, a white opaque gel is obtained. Grafting the gelling block (4) on the diacid polyester (5), perfectly soluble in oils, is therefore necessary to afford transparency of the gels.

Preparation 3: Preparation of the diamine functionalized precursor (4) from 1 equivalent of diacid (2) for 1 equivalents of diamine (3).

The diamine functionalized precursor is prepared from sebacic acid and Priamine 1075®.

26.67 g of Priamine 1075® and 10.00 g of sebacic acid are introduced into a 100 mL flask. The reaction mixture is left under magnetic stirring at 140° C. for 6 h under vacuum. 2.65 g of Priamine 1075® are added to the reaction medium as a termination agent, and then the reaction is continued for 6 h under vacuum. The reaction is monitored by infrared, in particular by increase and stabilization of the peak related to the amide functions (C═O, 1636 cm -1). Stearic exclusion chromatography (SEC) in polystyrene calibration indicates a number average molar mass (Mn) of 1980 g/mol.

Preparation 4: (SNO19019): Preparation of the diamine functionalized precursor (4) from 1 equivalent of diacid (2) for 2.5 equivalents of diamine (3).

The diamine functionalized precursor is prepared from sebacic acid and Priamine 1075®.

508.50 g of Priamine 1075® and 76.26 g of sebacic acid are introduced into a 1 L reactor. The reaction mixture is left under mechanical stirring at 140° C. for 12 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 540 g/mol.

A gelling test was implemented. The gel is produced at a concentration of 5% by weight of the product obtained in CCT (caprylic/capric triglyceride). 0.49 g of the end product is introduced and supplemented by 9.50 g of CCT in a 20 mL pill container. The crimped pill container is placed in a horizontal stirrer preheated to 80° C. and stirred for 30 min. After 24 h at ambient temperature, a white opaque gel is obtained. Grafting of the gelling block (4) onto the diacid polyester (5), perfectly soluble in oils, is therefore necessary to afford transparency of the gels.

Preparation 5 (SNO19043): Preparation of the diamine functionalized precursor (4) from 1 equivalent of diacid (2) for 2.5 equivalents of diamine (3).

The diamine functionalized precursor is prepared from sebacic acid and Priamine 1075®.

464.38 g of Priamine 1075® and 69.0 g of sebacic acid are introduced into a 1 L reactor. The reaction mixture is left under mechanical stirring at 140° C. for 12 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 540 g/mol.

Preparation 6: Preparation of the diamine functionalized precursor (4) from 1 equivalent of diacid (2) for 2.5 equivalents of diamine (3).

The diamine functionalized precursor is prepared from succinic acid (Sigma Aldrich) and Priamine 1075®.

34.29 g of Priamine 1075® and 2.998 g of succinic acid are introduced into a 100 mL flask. The reaction mixture is left under magnetic stirring at 180° C. for 1 h under nitrogen flow and then 3 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 540 g/mol.

Preparation 7: Preparation of the diamine functionalized precursor (4) from 1 equivalent of diacid (2) for 2.5 equivalents of diamine (3).

The diamine functionalized precursor is prepared from adipic acid (Sigma Aldrich) and Priamine 1075®.

27.78 g of Priamine 1075® and 3.01 g of adipic acid are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 570 g/mol.

Preparation 8: Preparation of the diamine functionalized precursor (4) from 1 equivalent of diacid (2) for 2.5 equivalents of diamine (3).

The diamine functionalized precursor is prepared from itaconic acid (Sigma Aldrich) and Priamine 1075®.

31.10 g of Priamine 1075® and 3.01 g of itaconic acid are introduced into a 100 mL flask. The reaction mixture is left under magnetic stirring at 140° C. for 7 h under vacuum then at 180° C. for 3 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 570 g/mol.

Preparation 9: Preparation of the diamine functionalized precursor (4) from 1 equivalent of diacid (2) for 2.5 equivalents of diamine (3).

The diamine functionalized precursor is prepared from furandicarboxylic acid (FDCA) (Sigma Aldrich) and Priamine 1075®.

In a 100 mL flask, 3.23 g of FDCA is dispersed hot (100° C.) in 28 g of butanol, and then 28 g of Priamine 1075® is added. The mixture is next heated at 140° C. under vacuum for 24 h. The butanol is distilled and recovered by means of an assembly of the Dean-Stark type. The mixture is next placed at 200° C. under vacuum for 8 h. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 680 g/mol.

Example 1: Preparation of a Polyamide (1) From a Diacid Polyester (PRICA®) (5) and the Diamine Functionalized Precursor (4) (Preparation 1)

24.00 g of PRICA 2405® and 6.28 g of the precursor synthesized in preparation 1 are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 5900 g/mol.

A gelling test was implemented. The gel is produced at a concentration of 5% by weight of the product obtained in CCT. 0.3334 g of a sampling made at the end of 4 h of reaction is introduced and supplemented up to 6.667 g with CCT in a 10 mL pill container. 0.337 g of the end product (24 g of reaction) is introduced and supplemented up to 6.740 g with CCT in a 10 mL pill container. The crimped pill containers are placed in a horizontal stirrer preheated to 100° C. and stirred for 30 min. After 24 h at ambient temperature, translucent gels are obtained.

Example 2: Preparation of a Polyamide (1) From a Diacid Polyester (PRICA®) (5) and the Diamine Functionalized pPecursor (4) (Preparation 2)

24.03 g of PRICA 2405® and 5.84 g of the precursor synthesized in preparation 2 are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 6100 g/mol.

A gelling test was implemented. The gel is produced at a concentration of 5% by weight of the product obtained in CCT. 5.00 g of the end product and 95.01 g of CCT are introduced into a 150 mL beaker. The beaker is placed in a bain marie preheated to 180° C. and mechanical stirring is initiated at 200 rpm when the temperature of the content of the beaker reaches 95° C. and is then increased to 300 rpm when the content of the beaker reaches 98° C. Stirring is maintained for 30 min at 100±2° C. The content of the beaker is poured into two plastic pots. After 24 h, the gels obtained are transparent.

Example 3: Preparation of a Polyamide (1) From a Diacid Polyester (PRICA®) (5) and the Diamine Functionalized Precursor (4) (Preparation 3)

24.01 g of PRICA 2405® and 7.46 g of the precursor synthesized in preparation 3 are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$).

A gelling test was implemented. The gel is produced at a concentration of 5% by weight of the product obtained in CCT. 0.355 g of the end product (24 h of reaction) is introduced and supplemented up to 7.079 g with CCT in a 10 mL pill container. The crimped pill container is placed in a horizontal stirrer preheated to 100° C. and stirred for 30 min. After 24 h at ambient temperature, the gel obtained is cloudy.

Example 4 (SNO19025): Preparation of a Polyamide (1) From a Diacid Polyester (PRICA®) (5) and the Diamine Functionalized Precursor (4) (Preparation 4)

751.96 g of PRICA 2405® and 146.53 g of the precursor synthesized in preparation 4 are introduced into a 1.7 L reactor. The reaction mixture is left under magnetic stirring at 140° C. for 4.5 h under vacuum. The reaction is monitored by infrared, in particular by increase and stabilization of the peak related to the amide functions (C═O, 1637 $cm^{-1}$). Stearic exclusion chromatography (SEC) in polystyrene calibration indicates a number average molar mass (Mn) of 2500 g/mol (Mp 7060 g/mol).

Gelling tests were implemented. The gels are produced at the concentrations of 4%, 5% and 10% by weight of the product obtained in CCT. The end product is introduced and supplemented with CCT in a 20 mL pill container. The crimped pill container is placed in a horizontal stirrer preheated to 80° C. and stirred for 30 min. The gels obtained are transparent after 24 h.

Example 5 (SNO19046): Preparation of a Polyamide (1) From a Diacid Polyester (PRICA®) (5) and the Diamine Functionalized Precursor (4) (Preparation 5)

523.07 g of PRICA 2405® and 103.01 g of the precursor synthesized in preparation 5 are introduced into a 1 L reactor. The reaction mixture is left under magnetic stirring at 140° C. for 4.5 h under vacuum. The reaction is monitored by infrared, in particular by increase and stabilization of the peak related to the amide functions (C═O, 1637 $cm^{-1}$). Stearic exclusion chromatography (SEC) in polystyrene calibration indicates a number average molar mass (Mn) of 2800 g/mol (Mp 7300 g/mol).

Gelling tests were implemented. The gels are produced at the concentrations of 4% and 10% by weight of the product obtained in CCT. The end product is introduced and supplemented with CCT in a 20 mL pill container. The crimped pill container is placed in a horizontal stirrer preheated to 80° C. and stirred for 30 min. The gels obtained are transparent after 24 h.

Example 6 (SNO19024): Preparation of a Polyamide (1) From a Diacid Polyester (PRICA®) (5) and the Diamine Functionalized Precursor (4) (Preparation 4)

12.51 g of PRICA 2405® and 2.34 g of the precursor synthesized in preparation 4 are introduced into a 100 mL flask. The reaction mixture is left under magnetic stirring at 140° C. for 4 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 3300 g/mol (Mp 8100 g/mol).

Example 7 (SNO19014): Preparation of a Polyamide (1) From a Diacid Polyester (PRICA®) (5) and the Diamine Functionalized Precursor (4) (Preparation 2)

30.0 g of PRICA 2405® and 7.50 g of the precursor synthesized in preparation 2 are introduced into a 100 mL flask. The reaction mixture is left under magnetic stirring at 140° C. for 4 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 2800 g/mol (Mp 7300 g/mol).

Example 8: Preparation of a Polyamide (1) From a Diacid Polyester (PRICA®) (5) and the Diamine Functionalized Precursor (4)

24.01 g of PRICA 2405® and 3.11 g of the precursor synthesized in preparation 2 are introduced into a 100 mL flask. The reaction mixture is left under magnetic stirring at 140° C. for 4 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 5600 g/mol.

A gelling test was implemented. The gel is produced at a concentration of 5% by weight of the product obtained in CCT. 0.341 g of the end product (4 h of reaction) is supplemented up to 6.84 g with CCT in a 10 mL pill container. The crimped pill container is placed in a horizontal stirrer preheated to 80° C. and stirred for 30 min. After 24 h at ambient temperature, a perfectly transparent gel is obtained.

Example 9: Preparation of a Polyamide (1) From a Diacid Polyester (PRICA®) (5) and the Diamine Functionalized Precursor (4)

18.42 g of PRICA 2405® and 8.02 g of the precursor synthesized in preparation 2 are introduced into a 100 mL flask. The reaction mixture is left under magnetic stirring at 140° C. for 24 h under vacuum. The reaction is monitored by infrared, in particular by increase and stabilization of the peak related to the amide functions (C═O, 1636 $cm^{-1}$). Stearic exclusion chromatography (SEC) in polystyrene calibration indicates a number average molar mass (Mn) of 5600 g/mol.

A gelling test was implemented. The gel is produced at a concentration of 5% by weight of the product obtained in CCT. 0.338 g of the end product is supplemented up to 6.86 g with CCT in a 10 mL pill container. The crimped pill container is placed in a horizontal stirrer preheated to 80° C. and stirred for 30 min. After 24 h at ambient temperature, a cloudy gel is obtained.

Example 10: Preparation of a Polyamide From a Diacid Polyester (PRICA®) (5) and a Diamine (Priamine®) (3)

25.10 g of PRICA 2405® and 2.62 g of Priamine 1075® are introduced into a 100 mL flask. The reaction mixture is left under magnetic stirring at 140° C. for 4 h under vacuum. The reaction is monitored by infrared, in particular by increase and stabilization of the peak related to the amide functions (C═O, 1636 $cm^{-1}$).

A gelling test was implemented. The gel is produced at a concentration of 5% by weight of the product obtained in CCT. 0.50 g of the end product (4 h of reaction) is introduced and supplemented up to 10.01 g with CCT in a 20 mL pill container. The crimped pill container is placed in a horizontal stirrer preheated to 80° C. and stirred for 30 min. After 24 h at ambient temperature, the solution is transparent but is not gelled. The use of a gelling block (4) is therefore necessary for obtaining polyamide gelling oils.

Example 11: Gelling Tests on Various Oils Implemented With the Synthesized Gelling Polyamides (5% by weight)

The polyamide (1) used for the gelling tests comes from 0.55 equivalent of the gelling precursor (4), consisting of one equivalent of sebacic acid (2) for 2.5 equivalents of Priamine 1075® (3), and one equivalent of PRICA 2405® (5).

The results are set out in table 1 below. The oils are identified by their INCI name.

The gelling agent was solubilized in oil at 80° C. under stirring.

The strength of the gels was evaluated as follows: the transparency of the gels is evaluated qualitatively, by observing a pill container containing some gel. If it is possible to read written characters very clearly through the pill container, then the gelling agent is considered to form transparent gels. The gel is considered to be strong if it does not flow when the pill container is turned over and weak if the surface of the sample deforms or if the gel flows.

TABLE 1

| INCI | Gel | Transparency |
|---|---|---|
| HELIANTHUS ANNUUS SEED OIL | strong | Translucent |
| GLYCINE SOJA OIL | strong | Translucent |
| SESAMUM INDICUM SEED OIL | strong | Translucent |
| PRUNUS AMYGDALUS DULCIS OIL | strong | Translucent |
| SIMMONDSIA CHINENSIS SEED OIL | strong | Translucent |
| OLEA EUROPAEA FRUIT OIL | strong | Translucent |
| VITIS VINIFERA SEED OIL | strong | Translucent |
| PUNICA GRANATUM SEED OIL | strong | Translucent |
| CORYLUS AVELLANA SEED OIL | strong | Translucent |
| PRUNUS DOMESTICA SEED OIL | strong | Translucent |
| RICINUS COMMUNIS SEED OIL | strong | Transparent |
| TRITICUM VULGARE GERM OIL | strong | Translucent |
| OCTYLDODECANOL | strong | Transparent |
| ETHYLHEXYL PALMITATE | strong | Transparent |
| COCO-CAPRYLATE | weak | Transparent |
| CAPRYLIC/CAPRIC TRIGLYCERIDE | strong | Transparent |

Example 12: Measurement of the Viscosity of Gels Produced in Caprylic/Capric Triglyceride With the Polyamides of Examples 1, 2, 4 and 5 at a Concentration of 5% by Weight The viscosity measurements were made with a TA Instruments AR1500ex viscometer by oscillatory rheology measurement, at a temperature of 25° C., at an oscillation force of 1 Pa and at a frequency of 1 Hz.

TABLE 2

| Samples | SOV18028 Example 1 | SOV19014 Example 2 | SOV19007 Example 3 | SOV19016-2 Example 9 |
|---|---|---|---|---|
| Viscosity (Pa · s) | 11.4 | 2.7 | 0.5 | 38.8 |

Example 13: Preparation of a Polyamide (1) From a Diacid Polyester (PRICA®) (5) and the Diamine Functionalized Precursor (4) (Preparation 7)

20.00 g of PRICA 2405® and 7.55 g of the precursor (4) synthesized in preparation 7 are introduced into a 100 mL flask. The reaction mixture is left under magnetic stirring at 140° C. for 4 h under vacuum. The reaction is monitored by infrared, in particular by increase and stabilization of the peak related to the amide functions (C═O, 1636 $cm^{-1}$).

A gelling test was implemented. The gel is produced at a concentration of 5% by weight of the product obtained in CCT. 0.50 g of the end product is introduced and supplemented up to 10.01 g with CCT in a pill container. The crimped pill container is placed in a horizontal stirrer heated at 80° C. for 30 min. After 24 h, the mixture is gelled and is perfectly transparent.

Example 14: Termination of the Chains of the Gelling Compound (1) by Means of a Hydroxylated Compound (6)

20.00 g of the gelling compound (1) (identical to example 2) and 1.00 g of cetyl alcohol (Evonik) are introduced into a first 100 mL flask. In a second 100 mL flask, fulfilling the role of control, 15.39 g of the gelling compound (1) is introduced. The reaction mixtures are left under magnetic stirring at 200° C. for 1 h 30 under vacuum. The reactions are monitored by infrared, in particular by increase and stabilization of the peak related to the ester function (C═O, 1730 $cm^{-1}$).

Gelling tests were implemented. The gels are produced at a concentration of 5% by weight of the product obtained in sunflower oil (INCI : Helianthus Annuus seed oil). 0.50 g of the end product terminated by cetyl alcohol and 9.50 g of sunflower oil are introduced into a pill container. 0.51 g of the control end product and 9.15 g of sunflower oil are introduced into a second pill container. The crimped pill containers are placed in a horizontal stirrer heated at 80° C. for 30 min. After 24 h, the mixtures are gelled and the pill container containing the product terminated by cetyl acid is transparent while the pill container containing the reference product is translucent.

Example 15: Comparison of the Properties of the Polyamide Compound (1) of Example 4 (SNO19025) With Commercially Available Gelling Compounds Each gelling agent was dissolved in caprylic/capric triglyceride oil (CCT) following the protocol proposed by the supplier.

Each mixture is then evaluated on the next day with regard to:

- its organoleptic characteristics, its visual appearance, its transparency, its color, its homogeneity, and
- its sensory properties, by directly touching a blob of gel on the hand.

The results set out in table 3 below make it possible to compare the proportion of content of natural origin (naturalness) of the gelling agent, its ability to form a gel, the appearance of the gel, its transparency and its sensory nature (texture) when this was evaluated.

TABLE 3

| INCI | Proportion of content of natural origin | % gelling agent | Operating method | Appearance | Texture |
|---|---|---|---|---|---|
| Compound (1) example 4 SNO19025 | 100% | 4 | 30 min deflocculator 80° C. 300 rpm | Transparent thick gel Shape memory * | Smooth feel powdery finish |
| Silica dimethyl silylate | 0% | 2.6 | 15 min deflocculator 80° C. 700 rpm | Transparent gel Fluid deposit | Dry crunchy feel |
| Helianthus Annuus seed oil, Caprylic/capric triglyceride, Styrene/ butadiene copolymer | 0% (Polymer) | 13 | 15 min deflocculator 60° C. 700 rpm | Transparent liquid gel | |
| Polyurethane-79 | 0% | 5 | 30 min deflocculator 95° C. 700 rpm | Transparent thick gel | Dry light feel |
| Caprylic/capric triglyceride, Stearalkonium Bentonite, Propylene carbonate | Partially biosourced | 12 | 15 min deflocculator 70° C. 700 rpm | Liquid greenish opaque gel | |

TABLE 3-continued

| INCI | Proportion of content of natural origin | % gelling agent | Operating method | Appearance | Texture |
|---|---|---|---|---|---|
| Polyamide-8 | Partially biosourced | 5 | 25 min deflocculator 80° C. 700 rpm + 20 min rotor stator 15000 rpm | Thick opaque white gel | |
| Dextrin palmitate | 100% | 5 | 30 min deflocculator 80° C. 700 rpm | Thick opaque gel | Dry powdery feel |
| Trihydroxystearin | 100% | 3 | 65 min deflocculator 50° C. 700 rpm | Fluid opaque white gel | |
| Castor oil/IPDI copolymer | 91% | 5 | 30 min deflocculator 100° C. 700 rpm | Transparent thick gel | Soft light feel |

* Shape memory: The texture of the gel re-forms after crushing

The results show that compound (1) according to the invention makes it possible to combine the properties of transparency and non-granular feel by using a completely biosourced polymer in the solution state at low temperature (at 80° C.).

The non-biosourced gelling agents (2$^{nd}$, 3$^{rd}$ and 4$^{th}$ gelling agents tested) have the following disadvantages:

- The silica derivatives require a high percentage for use thereof and have an unpleasant feel judged to be "crunchy".
- The "styrene copolymers" are not adapted to the application sought because, as use of the pure polymer requires a great deal of energy, the products available are always in solution.
- Polyurethane-79 requires a high temperature (95° C.) for optimal use and the gels obtained lack stability over time.

Among the alternatives of natural origin existing on the market, none makes it possible to form transparent gels under the tested conditions.

Example 16: GellingProperties With Respect to Various Oils

The gelling polyamide of example 7 (SNO19014) was introduced at a concentration by weight of 2% into various oils, and then stirred at 80° C. for 30 min. The results are set out in table 4 below.

Each mixture is evaluated visually the next day on its gel appearance or not (the pill container is turned over, if the product is a gel then the product does not flow), its transparency or its cloudiness by means of a cross-ruled sheet arranged at the rear of the pill container.

TABLE 4

| INCI | Obtains a gel | Appearance |
|---|---|---|
| Ethylhexyl palmitate | yes | clear |
| Caprylic/capric triglyceride | yes | clear |
| Helianthus annuus (sunflower) oil | yes | clear |
| Castor oil | yes | clear |
| Coconut oil | yes | clear |
| Glycine soya oil | yes | cloudy |
| Ethylhexyl methoxy cinnamate | yes | clear |
| Ethylhexyl Methoxycrylene | yes | opaque |
| Ethylhexyl salicylate | yes | clear |
| Homosalate | yes | clear |
| Octocrylene | yes | opaque |
| Isopropyl myristate | yes | clear |
| Coco caprylate | yes | clear |
| Dicaprylyl carbonate | yes | clear |
| Dimethicone | no | cloudy |
| Coco-caprylate/caprate | yes | clear |
| Ethyl oleate | yes | clear |
| Prunus domestica | yes | cloudy |
| Corylus avellana seed oil | yes | cloudy |

The results show that the gelling polyamide according to the invention makes it possible to form a transparent gel in 13 of the oils tested and to form a non-transparent gel in 5 of the oils tested.

The gelling polyamide according to the invention makes it possible to gel in particular polar oils: vegetable oils, esters and most of the organic sunscreens.

Example 17: Study of Gelling Capability in caCrylic/Capric Triglyceride Oil

The gelling polyamide of example 5 (SNO19046) was introduced at increasing concentrations by weight (from 0.5% to 10% by weight) in caprylic/capric triglyceride oil containing nacres, and then stirred at 80° C. for 30 min by means of a deflocculator at 300 rpm.

Each mixture is evaluated visually the next day with respect to its organoleptic characteristics, its appearance, its transparency, its color and its homogeneity.

The viscosity is measured by means of a Brookfield LVDVII+ viscometer equipped with a Helipath module at a speed of 10 revolutions per minute. The measurement is made after one minute of crushing. The results are set out in tables 5 and 6.

The suspension capability was also measured with respect to nacres, as well as the ability of the gelled mixture for being sprayed (sprayability).

"Suspension capability" means the ability to maintain solids in suspension in the medium without precipitation occurring over time. This ability is evaluated visually just after preparation, and then confirmed the day after the gel was prepared, the quantity of nacres present at the bottom of the pill container then being visually evaluated.

TABLE 5

| | % of gelling compound (example 5) | | | |
|---|---|---|---|---|
| | 0.5 | 1 | 2 | 4 |
| 24 h viscosity (Pa · s) | 0.50 | 1.00 | 1.75 | 3.60 |
| Appearance | transparent clear gel | very clear and homogeneous gel | very clear and homogeneous gel | very clear slightly yellow gel |
| Suspension capability (0.05% nacre) | immediate | immediate | immediate | immediate |
| Sprayability | yes | yes | yes | yes |

TABLE 6

| | % of gelling compound (example 5) | | |
|---|---|---|---|
| | 6 | 8 | 10 |
| 24 h viscosity (Pa · s) | 6.00 | 8.10 | 9.70 |
| Appearance | very clear slightly yellow gel | very clear slightly yellow gel | very transparent gel |
| Suspension capability (0.05% nacre) | immediate | immediate | immediate |
| Sprayability | yes | yes with unidirectional jet | difficult to spray |

The suspension capability of the gel formed by the invention is immediate, as from 60° C. during the protocol, and this as from 0.5% polyamide.

The galenic formulation of the gel formed makes it possible to be sprayed by means of a spray easily up to at least 6% gelling polyamide.

The setting of the gel over time was next evaluated for the gel at 6% gelling polyamide in caprylic/capric triglyceride oil. The viscosity was measured by means of a Brookfield LVDVII+ viscometer and with a Helipath module at a speed of 10 rpm, the measurement being made after one minute. The measurements were next made at 30 min, 1 h, 2 h, 4 h, 6 h, 8 h, 24 h, 30 h and 48 h after preparation. The viscosity measured is 6.6 Pa·s after 4 h, 6.6 Pa·s after 8 h and 7 Pa·s after 48 h, showing that the gel forms quickly.

Example 18

The gel containing 4% of example 4 in caprylic/capric triglyceride is combined with ethanol at various percentages in order to check its compatibility therewith. The appearance and viscosity of the gel is evaluated.

TABLE 7

| | % ethanol | | | | |
|---|---|---|---|---|---|
| | 0 | 1 | 2 | 5 | 10 |
| Viscosity (Pa · s) | 3.6 | 2.3 | 1.3 | 0.65 | 0.35 |
| Appearance | Clear, homogeneous gel | Clear, homogeneous gel | Clear, homogeneous gel | Clear, homogeneous gel | Clear, homogeneous gel, very fluid |

The viscosity is measured by means of a Brookfield LVDVII+ viscometer and a Helipath module at a speed of 10 rpm, the measurement is taken after one minute. It is highly impacted as soon as 1% ethanol is added to the mixture.

Example 19: Compatibility With Waxes and Butters

The compatibility of the gelling agent with waxes and butters is evaluated. A gel containing 4% polyamide of example 4 (SNO19025) is tested in combination with various waxes. Each test is prepared in the following manner: a reference containing the wax to be evaluated at 4% in caprylic/capric triglyceride, a test containing the wax to be evaluated, 4% gelling agent of example 4 and the caprylic/capric triglyceride oil. The tests are prepared on 10 g and heated at 80° C. for 30 min under mechanical stirring.

Each mixture is evaluated visually the next day with regard to its organoleptic characteristics, its visual appearance, its transparency by means of a square-ruled paper at the rear of the pill container, its color and its homogeneity.

The results are set out in table 8.

TABLE 8

| INCI | Gel appearance without gelling agent | Gel appearance with gelling agent |
|---|---|---|
| Hydrogenated coco-glycerides | homogeneous clear liquid | homogeneous clear gel |
| C10-18 triglycerides | homogeneous clear liquid | homogeneous clear gel |
| Shea butter | homogeneous clear liquid | homogeneous clear gel |
| Cera alba | homogeneous opaque solid | homogeneous opaque solid |
| Behenyl alcohol | homogeneous opaque gel | homogeneous opaque solid |
| Cetyl alcohol | homogeneous clear liquid | homogeneous clear gel |
| Glyceryl stearate | homogeneous opaque gel | homogeneous yellow slightly opaque gel |
| Myristyl miristate | homogeneous clear liquid | homogeneous clear gel |
| Paraffin wax | homogeneous white solid | homogeneous beige gel |
| Cetyl stearyl alcohol | homogeneous clear liquid | homogeneous clear gel |
| Oryza sativa oil | homogeneous opaque liquid | homogeneous opaque weak gel |
| Helianthus annuus seed cera | opaque thick gel | homogeneous opaque thick gel |
| C18-36 Acid Triglyceride | opaque thick gel | homogeneous opaque thick gel |

The results show that the presence of the gelling polyamide according to the invention makes it possible to obtain a more viscous, more homogeneous and smoother mixture.

Example 20: Compatibility With Surfactants

Compatibility with surfactants was tested in the same way as for the waxes and butters in example 22. The results are set out in table 9.

TABLE 9

| INCI | appearance of gel without gelling agent of the invention | appearance of gel with gelling agent of the invention |
|---|---|---|
| PEG-40 sorbitan peroleate | clear and homogeneous liquid | homogeneous clear gel |
| PEG-20 Glyceryl Triisostearate | clear and homogeneous liquid | homogeneous clear gel |
| Polyglyceryl-3 Oleate | clear and homogeneous liquid | homogeneous clear gel |
| Polyglyceryl-4 isostearate | clear and homogeneous liquid | homogeneous clear gel |

The results show that, for all the materials tested, the mixture is gelled by the polymer of the invention and is homogeneous. These ingredients are clearly compatible.

Example 21: Suspension Capability With Various Fillers

The suspension capability of the gelling polymer of example 4 was evaluated with various fillers: pigments, powder and exfoliant.

These fillers are each tested at a concentration by weight of 5% in the same basic gel containing 4% by weight gelling agent of example 4 (SNO19025) in caprylic/capric triglyceride oil.

The polyamide is added to the oil, heated at 80° C. under stirring of 300 rpm by means of a deflocculator blade for 30 min, the mixture is next cooled and the fillers are added under the same stirring at a temperature of 40° C.

Each mixture is next evaluated the next day with regard to:

its organoleptic characteristics, its visual appearance, its transparency, its color and its homogeneity, its viscosity measured by means of a Brookfield LVDVII+ viscometer and a Helipath module at a speed of 10 rpm, the measurement being taken after one minute.

TABLE 10

| INCI | Appearance | Viscosity (93) 10 rpm 1 min (Pa · s) |
|---|---|---|
| Titanium dioxide, silica (UV filter) | clear fluid gel | 1.5 |
| Titanium dioxide (pigment) | block gel | 3.2 |
| Sugar | gel with deposit of sugar | 3.3 |
| Mica (78-88%) and titanium dioxide (pigment) | nacreous gel | 3.5 |
| Clay | black gel | 3.2 |
| Volcanic sand (sand) | gel with grain gradient | 2.58 |
| Luffa cylindrica fruit (exfoliant) | homogeneous gel | 4.93 |
| Cellulose acetate (exfoliant) | homogeneous gel | 3.82 |
| Vaccinium macrocarpon fruit powder (exfoliant) | thick gel | 4.40 |

The results show that the gel with 4% gelling polyamide according to the invention makes it possible to immediately suspend all the fillers during manufacture. The gelling polyamide according to the invention can therefore be used in cosmetic formulae containing fillers and powders.

Example 22: Study of Transparency and Viscosity

The measurements were made on the gels obtained with the compounds (1) of examples 4 and 5 in caprylic/capric triglyceride oil, at a concentration of 4% by weight.

The measurements were made as follows:

The viscosity measurements were made with a TA Instruments AR1500ex viscometer by oscillation rheology measurement, as a temperature of 25° C., at an oscillation force of 1 Pa and at a frequency of 1 Hz.

The transparency measurement was made on a polymer gel (example 4 SNO19025, example 5 SNO19046 and dextrin palmitate) in a vegetable oil (caprylic/capric triglyceride or sunflower oil) with a Hanna Instruments HI 88713 turbidity meter at a temperature of 25° C. and expressed in "NTU" turbidity unit prescribed by the Environmental Protection Agency (Nephelometric Turbidity Unit).

For comparative purposes, the transparency was measured on the dextrin palmitate gel in 4% by weight caprylic/capric triglyceride. This gel is opaque by observation with the naked eye.

TABLE 11

| Example | Oil | Concentration % by weight | Viscosity, Pa · s (oscillation, 25° C., 1 Hz, 1 Pa) | Transparency, NTU |
|---|---|---|---|---|
| Example 4 (SNO19025) | Caprylic/capric triglyceride | 4 | 1.08 | 5 |
| | Caprylic/capric triglyceride | 10 | 3.4 | 13 |
| | Helianthus annuus seed oil (sunflower oil) | 4 | 1.5 | 6 |
| Example 5 (SNO19046) | Caprylic/capric triglyceride | 4 | 1.7 | 12 |
| | Caprylic/capric triglyceride | 10 | 6.3 | 13 |
| — (control) | Caprylic/capric triglyceride | 0 | 0.02 | 0.1 |
| — (control) | Helianthus annuus seed oil (sunflower oil) | 0 | 0.06 | 0.2 |
| Comparative example dextrin palmitate (Rheopearl KL 2) | Caprylic/capric triglyceride | 4 | — | 2760 |

Example 23: Incorporation of the Gelling Polyamide (1) in Cosmetic Formulations The gelling polyamide obtained in example 2 was incorporated in cosmetic formulations.

1) Gelling of the Sunflower Oil Containing a Perfume in a Small Proportion (0.5% m)

In a beaker, 96.51 g of sunflower oil and 3.00 g of the gelling polyamide (1) are introduced, heated at 80° C. under mechanical stirring (300 rpm) for 20 min. The homogeneous mixture obtained is cooled to 50° C. and 0.49 g of perfume is added. After 24 h at ambient temperature, the mixture is homogeneous and gelled and has a viscosity of 22.7 Pa·s.

2) Suspension of Nacres in the Sunflower Oil.

In a beaker, 96.60 g of sunflower oil, 2.02 g of gelling polyamide (1) and 1.00 g of nacres are introduced, heated at 80° C. under mechanical stirring (300 rpm) for 20 min. The homogeneous mixture obtained is cooled to 50° C. and 0.52 g of perfume is added. After 24 h at ambient temperature, the mixture is homogeneous, the nacres are uniformly distributed in the medium, and has a viscosity of 13.5 Pa·s.

3) Suspension of Exfoliating Beads in the Sunflower Oil.

In a beaker, 97.40 g of sunflower oil, 2.00 g of gelling polyamide (1) and 0.10 g of exfoliating beads are introduced and heated at 80° C. under mechanical stirring (300 rpm) for 20 min. The homogeneous mixture obtained is cooled to 50° C. and 0.52 g of perfume is added. After 24 h at ambient temperature, the mixture is homogeneous, the beads are uniformly distributed in the medium, and has a viscosity of 14.5 Pa·s.

4) Suspension of Titanium Dioxide in the Sunflower Oil.

In a first beaker, 52.56 g of sunflower oil and 25.00 g of titanium dioxide are introduced and dispersed by means of a high-shear mixer for 5 min at ambient temperature. In a second beaker, 20.00 g of sunflower and 2.00 g of the gelling polyamide (1) are introduced and mixed for 15 min at 80° C. under mechanical stirring (300 rpm). This beaker is introduced into the first beaker, previously heated to 80° C. under mechanical stirring (300 rpm), and the stirring is maintained for an additional 10 min. The homogeneous mixture obtained is cooled to 50° C. and 0.50 g of perfume is added. After 24 h at ambient temperature, the mixture is homogeneous, the particles of titanium dioxide are uniformly distributed in the medium, and has a viscosity of 55 Pa·s.

5) Water in Oil Emulsion.

In a first beaker, 72.03 g of sunflower oil and 4.00 g of emulsifier (Easynov) and 4.00 g of gelling polyamide (1) are introduced, heated to 80° C. and mixed by means of a mechanical stirrer (300 rpm). In a second beaker, 110.00 g of demineralized water and 1.01 g of salt (NaCl) are introduced and mixed for 5 min at 70° C. under mechanical stirring (300 rpm). This beaker is introduced into the first beaker dropwise and stirring is maintained until the solution cools to 50° C., where 0.50 g of perfume is added. A homogeneous mixture is obtained. After 24 h at ambient temperature, the mixture is homogeneous and gelled.

6) Gelling of a Perfume

In a beaker, 70.00 g of sunflower oil and 10.00 g of the gelling polyamide (1) are introduced, and heated at 80° C. under mechanical stirring (300 rpm) for 20 min. The homogeneous mixture obtained is cooled to 50° C. and 19.94 g of perfume is added. The stirring is maintained for 2 min. After 24 h at ambient temperature, the mixture is homogeneous and gelled and has a viscosity of 65 Pa·s.

7) Transparent Anti-Aging Gel

A complete formula was prepared containing the gelling polyamide of example 4:

TABLE 12

| INCI | % |
|---|---|
| Caprylic capric triglycerides | 88.3 |
| Compound of example 4 (SNO19025) | 6 |
| Simmondsia chinensis oil | 5 |
| Perfume | 0.5 |
| dl-α-tocopheryl acetate | 0.2 |

The gel is thick and smooth, perfectly transparent. Its viscosity at D+1 is 5.2 Pa·s.

The polyamide according to the invention makes it possible to form a texture that is easy to offer in a tube or bottle, easy to spread and soft to the touch.

8) Face-Nourishing Nacreous Spray Fluid

A more fluid formula containing the gelling polyamide of example 4 is produced with nacres in suspension.

TABLE 13

| INCI | % |
|---|---|
| Caprylic capric triglycerides | 93.5 |
| Compound of example 4 (SNO19025) | 1 |
| Simmondsia chinensis oil | 5 |
| Perfume | 0.5 |
| Mica, titanium dioxide | 0.5 |
| dl-α-tocopheryl acetate | 0.2 |

This formula is very fluid and the nacres are maintained in suspension at D+1.

Its viscosity is less than 0.5 Pa·s.

The polyamide of example 4 therefore makes it possible to maintain in suspension 0.5% nacreous fillers. This suspension capability is effective as soon as the polymer is used, and is immediate after preparation.

9) Sublimating Face Gel

Another nacreous gel containing the gelling polyamide of example 4, able to be presented in bottle or pot, was prepared.

TABLE 14

| INCI | % |
|---|---|
| Ethylhexyl palmitate | 44.1 |
| Isopropyl myristate | 50 |
| Mica, titanium dioxide | 0.2 |
| Compound of example 4 (SNO19025) | 5 |
| dl-α-tocopheryl acetate | 0.2 |
| Perfume | 0.5 |

This gel offers a dry powdery sensation, the gelling polyamide of example 4 here makes it possible to form a gel of moderate viscosity able to be presented in a bottle and to maintain the nacres in suspension effectively.

Its viscosity is 1.7 Pa·s at D+1.

The texture of this rather fluid gel re-forms after crushing like a shape-memory gel.

This allows a rather original application.

10) Nourishing Body Balm

A thick balm, dry to the touch, was prepared, containing the polyamide of example 4.

TABLE 15

| INCI | % |
|---|---|
| Ethylhexyl palmitate | 34.1 |
| Isopropyl myristate | 50 |
| Mica, titanium dioxide | 0.2 |

TABLE 15-continued

| INCI | % |
|---|---|
| Compound of example 4 (SNO19025) | 15 |
| dl-α-tocopheryl acetate | 0.2 |
| Perfume | 0.5 |

This strong gel has a soft dry feel. When crushed, the gel re-forms, reacting like a shape-memory gel. The polyamide of the invention makes it possible to gel the mixture strongly and to obtain a strong smooth gel.

This high percentage of polyamide is easy to implement. The nacres are well maintained in suspension and the viscosity is 6.0 Pa·s at D+1.

11) Oil in Water Emulsion

An emulsion was prepared with a continuous aqueous phase containing the polyamide of example 4.

TABLE 16

| INCI | % |
|---|---|
| Caprylic/capric triglycerides | 10 |
| C14-22 alcohols (and) C12-20 alkyl glucoside | 3 |
| Myristyl alcohol (and) myristyl glucoside | 0.5 |
| Compound of example 4 (SNO19025) | 5 |
| Water/Aqua | 72.2 |
| Propanediol | 2 |
| Xanthan gum | 0.2 |
| Glycerin | 3 |
| Pentylene glycol | 4 |
| Sodium phytate | 0.1 |

The viscosity is higher for the formula containing the gelling agent:

Reference viscosity=1.5 Pa·s/formula viscosity with the polyamide=2.3 Pa·s

Centrifuging the reference formula presents a phase difference of a few millimeters whereas the formula with the polyamide of the invention is stable and homogeneous.

The formula with the gelling polyamide is therefore more stable than the one that does not contain it. The gelling polyamide therefore makes it possible to stabilize the emulsions with continuous aqueous phase.

The feel of the cream that contains the polymer is richer and smoother and leaves a nourishing homogeneous film after spreading on the skin.

On the same basis, a CC cream containing 2% of a Sunshine Soft Bronze C84-6080® nacre (Sun Chemicals) was formulated. On application, the coverage of the color is improved in the presence of the gelling polyamide according to the invention and spreading is more precise. The formula containing the polyamide is also more stable over time than the reference formula that does not contain the gelling agent.

12) Water in Oil Emulsion No. 1

A water in oil emulsion containing the polyamide of example 4 is formulated with an emulsifier conventionally used in the formulae of this type.

TABLE 17

| INCI | % |
|---|---|
| Butyrospermum parkii butter | 5 |
| Polyglyceryl-2-dipolyhydroxystearate | 5 |
| Caprylic/capric triglyceride | 20 |
| Compound of example 4 (SNO19025) | 4 |
| Tocopheryl acetate | 0.3 |
| Aqua | 54.5 |

TABLE 17-continued

| INCI | % |
|---|---|
| Magnesium sulfate | 0.7 |
| Glycerin | 5 |
| Pentylene glycol | 5 |
| Perfume | 0.5 |

The emulsion produced with the gelling polyamide of example 4 is thicker than the reference formula without the polymer.

Reference: viscosity 6.4 Pa·s/test with polymer: viscosity 24.2 Pa·s.

The two formulae are stable under centrifugation and the emulsion has formed well.

The emulsion with the polyamide according to the invention is richer and more comfortable. The feel of the cream that contains the polyamide is richer and smoother and leaves a nourishing film on the skin after spreading.

13) Water in Oil Emulsion No. 2

Another type of water in oil emulsion was prepared.

TABLE 18

| INCI | % |
|---|---|
| Polyglyceryl-6 polyhydroxystearate (and) polyglyceryl-6 polyricinoleate | 3.50 |
| Coco-caprylate | 10.00 |
| Caprylic/capric triglyceride | 5.00 |
| Corylus avelanna oil | 5.00 |
| C10-18 Triglycerides | 5.00 |
| Compound of example 4 (SNO19025) | 6.00 |
| Aqua | 62.70 |
| Sodium chloride | 1.00 |
| Ethylhexylglycerin & phenoxyethanol | 0.80 |
| Perfume | 1.00 |

This emulsion is stable under centrifugation, is easy to sample and has a smooth spread. It leaves a rich film on the skin. The formula containing the polyamide of the invention is more stable than the one that does not contain it.

14) Water in Oil Foundation

Using the previous emulsion base, a water in oil foundation was prepared, containing 6% gelling polyamide of example 4.

TABLE 19

| INCI | % |
|---|---|
| Polyglyceryl-6 polyhydroxystearate (and) Polyglyceryl-6 polyricinoleate | 3.50 |
| Coco-caprylate | 5.00 |
| Caprylic/capric triglyceride | 5.00 |
| Corylus avelanna oil | 5.00 |
| C10-18 triglycerides | 5.00 |
| Compound of example 4 (SNO19025) | 6.00 |
| Aqua | 58.14 |
| Sodium chloride | 1.00 |
| Ethylhexylglycerin & phenoxyethanol | 0.80 |
| Perfume | 1.00 |
| Iron oxide white | 8 |
| Iron oxide yellow | 0.4 |
| Iron oxide red | 0.16 |
| Iron oxide black | 1 |

The emulsion has formed well, the pigments have integrated homogeneously in the emulsion. The color is homogeneous and the formula is stable under centrifugation.

The viscosity of this cream is 33.3 Pa·s.

The same emulsion produced without the gelling polyamide has a viscosity of 17 Pa·s.

The gelling polyamide of the invention therefore makes it possible to obtain a higher viscosity.

Adding the gelling polyamide makes it possible to obtain a localized application and shows good coverage of the color. The finish is more matt, the color more homogeneous than the reference cream without polyamide.

15) Lipstick

The gelling polyamide of the invention can also be incorporated in formulations of the stick type. A test containing 50% gelling polyamide of example 4 (SNO19025) in caprylic/capric triglyceride forms a very strong and transparent gel but too soft to be able to be presented in a stick. The film deposited on the lips is glossy, nourishing and comfortable. The taste of the stick thus formulated with the gelling polyamide is neutral.

By combining this gelling polyamide with another oil-gelling polymer, the castor oil/IPDI copolymer, a stick is obtained with acceptable strength and very transparent.

TABLE 20

| INCI | Formulation with the compound of example 4 % | Formulation with the compound of example 4 and castor oil/IPDI copolymer % |
|---|---|---|
| Caprylic/capric triglyceride | 43 | 43 |
| Dimer dilinoleyl dimer dilinoleate | 6 | 6 |
| Compound of example 4 (SNO19025) | 50 | 20 |
| Tocopherol acetate | 0.5 | 0.5 |
| Perfume | 0.5 | 0.5 |
| Titanium dioxide, mica | 0.6 | 0.01 |
| Castor oil/IPDI copolymer | 0 | 30 |

The formula combining the two polymers keeps the nacres in suspension homogeneously, the stick is indeed strong while allowing easy application of the product. The film deposited on the lips is glossy, nourishing and comfortable. The taste of the stick thus formulated with the gelling polyamide is neutral.

Associating the polyamide according to the invention with another polymer makes it possible to formulate a completely transparent stick that is sufficiently strong to be presented in a stick and sufficiently plastic to be applied easily to the lips.

16) Exfoliating Body Jelly

TABLE 21

| INCI | % |
|---|---|
| Caprylic/capric triglyceride | 75.45 |
| Compound of formula 4 (SNO19025) | 8.00 |
| Luffa cylindrica fruit | 4.00 |
| Vegetable wax | 2.00 |
| Polyglyceryl-3 oleate | 5.00 |
| Perfume | 0.50 |
| Tocopherol acetate | 0.05 |
| C10-18 triglycerides | 5.00 |

The polyamide of example 4 (SNO19025) makes it possible to gel the mixture and to keep the exfoliants in suspension. The gel is easy to spread and has a marked exfoliating action. It is easy to rinse and can be presented in a tube.

17) Sun Jelly With Zinc

Since the gelling polyamide of the invention has good suspension capability, it makes it possible to formulate water-free mineral sun products.

TABLE 22

| INCI | % |
|---|---|
| Zinc oxide (and) caprylic/capric triglyceride (and) polyhydroxystearic acid (and) polyglyceryl-3 polyricinoleate (and) isostearic acid (and) lecithin | 15 |
| Compound of example 4 (SNO19025) | 10 |
| Caprylic/capric triglyceride | 54.5 |
| Tocopherol acetate | 0.5 |
| Prunus domestica oil | 20 |

The gel is homogeneous and keeps the zinc oxide well in suspension. Smooth on application, it spreads well and deposits a soft powdery film.

18) Suncream With Organic Filters

The properties of the gelling polyamide according to the invention, namely:

- its high compatibility with UV protecting agents,
- its ability to stabilize emulsions,
- its easy homogeneous spread, and
- its ability to leave a homogeneous perceptible film on the skin, make it an advantageous ingredient in suncream formulae.

TABLE 23

| INCI | % |
|---|---|
| PEG-30 DIPOLYHYDROXYSTEARATE | 3 |
| POLYGLYCERYL-6 DIISOTEARATE | 2 |
| Compound of example 4 (SNO19025) | 4 |
| Dicaprylyl carbonate | 8 |
| Homosalate | 10 |
| Coco-caprylate/caprate | 6 |
| Ethylhexyl salicylate | 5 |
| Polysilicone-15 | 3 |
| Bis-ethylhexyloxyphenol methoxyphenyl triazine | 4 |
| Coco-caprylate | 8 |
| AQUA | 43 |
| GLYCERIN | 3 |
| MAGNESIUM SULFATE | 0.7 |
| TETRASODIUM EDTA | 0.05 |
| Phenoxyethanol, caprylyl glycol | 0.8 |
| Poloxamer 338, PPG12/SMDI copolymer | 0.3 |

This formula emulsifies easily, its viscosity is 4.0 Pa·s. The gelling polyamide participates in increasing the viscosity and stabilizing the emulsion formed. It is pleasant to spread and leaves a very soft protective film which is noticeable after application.

19) Suncream With Mineral Filters

A formulation of suncream is prepared using solely mineral filters of non-nanometric grade (i.e. where the primary particle size is not less than 100 nm).

TABLE 24

| INCI | % |
|---|---|
| Polyglyceryl-2, dipolyhydroxystearate | 4 |
| Shea butter | 1 |
| Caprylic/capric triglyceride | 25 |
| Compound of example 4 (SNO19025) | 6 |
| Titanium dioxide | 12 |
| Zinc oxide (and) caprylic/capric triglyceride (and) polyhydroxystearic acid (and) polyglyceryl-3 polyricinoleate (and) isostearic acid (and) lecithin | 23 |
| Aqua | 24 |
| Sodium chloride | 0.3 |
| Glycerin | 3 |
| Xanthan gum | 0.2 |
| Caprylhydroxamic acid (and) caprylyl glycol (and) propanediol | 1.5 |

The gelling polyamide participates in increasing the viscosity and stabilizing the emulsion formed. The highly natural emulsion forms very easily despite the very high concentration of mineral filters. This formula leaves a protective covering film on application.

20) Makeup-Removal Jelly

TABLE 25

| INCI | % |
|---|---|
| Coryllus avellana oil | 20 |
| Squalane | 10 |
| Caprylic/capric triglyceride | 41.3 |
| Compound of example 4 (SNO19025) | 5 |
| Methyl glucose dioleate | 10 |
| Tocopheryl acetate | 0.2 |
| Perfume | 0.5 |

The gel formed is completely transparent. Its texture is smooth and has a shape memory when crushed. It applies well to the face and easily removes makeup, even waterproof. Its film-forming ability facilitates makeup removal. The residue after makeup removal is easy to rinse with clear water.

21) Gloss

The gelling polyamide of the invention has after spreading a very glossy film-forming finish with high concentration and smoothness that make it an ingredient of choice for makeup products of the gloss type.

TABLE 26

| INCI | % |
|---|---|
| Ricinus communis seed oil | 34 |
| Isopropyl palmitate | 25 |
| Caprylic/capric triglyceride | 30 |
| Compound of example 4 (SNO19025) | 10 |
| Tocopherol acetate | 0.5 |
| Perfume | 0.5 |
| Mica, titanium dioxide | 0.05 |

The gel formed is easily formulated. It is perfectly transparent and homogeneous, makes it possible to keep nacres in suspension, is easily applied to the lips, it has a neutral taste and leaves a rich nourishing film on the lips.

The invention claimed is:

1. A polyamide Polyamide compound able to gel oils, of formula (1)

(1)

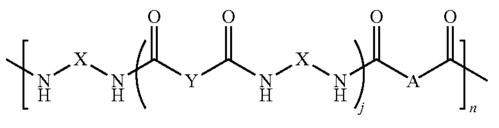

wherein

A =

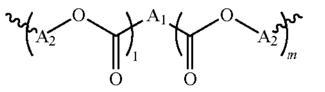

$A_1$ represents an alkyl radical, linear or branched, comprising from 2 to 40 carbon atoms, optionally from 2 to 12, said radical optionally comprising one or more unsaturations, being optionally interrupted by at least one heteroatom selected from O, N and S, and being optionally substituted by at least one —OAlk substituent, Alk representing an alkyl group comprising from 1 to 10 carbon atoms;

$A_2$ represents an alkyl radical, linear or branched, comprising from 2 to 30 carbon atoms, optionally from 5 to 22, said radical optionally comprising one or more unsaturations, and being optionally substituted by at least one —OAlk substituent, Alk representing an alkyl group comprising from 1 to 10 carbon atoms;

l and m represent, independently of each other, an integer from 1 to 20, optinally from 1 to 10, the sum l+m optionally being from 2 to 20;

n is an integer from 1 to 20, optionally from 2 to 8;

j is an integer from 1 to 10, optionally from 1 to 3;

X represents an alkyl radical, linear or branched, comprising from 2 to 60 carbon atoms, optionally 16 to 45 carbon atoms, said radical optionally comprising one or more unsaturations; and Y represents an alkyl radical, linear or branched, comprising from 3 to 35 carbon atoms, optionally from 6 to 18 carbon atoms.

2. The polyamide compound of formula (1) according to claim 1, wherein $A_1$ represents a linear alkyl radical comprising from 2 to 40, carbon atoms optionally from 2 to 12 carbon atoms, said radical optionally comprising one or more unsaturations.

3. The polyamide compound of formula (1) according to claim 1, wherein $A_2$ represents an alkyl radical, linear or branched, comprising from 5 to 18 carbon atoms, said radical optionally comprising one or more unsaturations, and optionally a group of formula

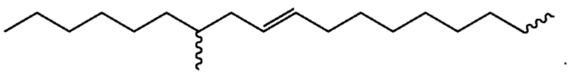

4. The polyamide compound of formula (1) according to claim 1, wherein the sum l+m has a mean value of 7, 11 or 15.

5. The polyamide compound of formula (1) according to claim 1, wherein:

$A_1$ represents a linear alkyl radical comprising 3 carbon atoms;

$A_2$ represents a branched alkyl radical comprising 17 carbon atoms;

l and m represent, independently of each other, an integer from 3 to 4, the sum l+m optionally being from 6 to 8;

n is an integer from 1 to 8, optionally from 1 to 3;

j is an integer from 1 to 10, optionally from 1 to 3;

X represents a branched alkyl radical comprising 36 carbon atoms; and

Y represents a linear alkyl radical comprising 8 carbon atoms.

6. A method for preparing a polyamide compound of formula (1)

(1)

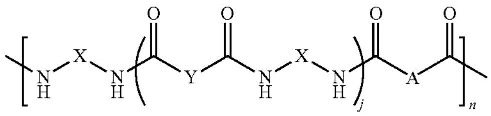

wherein

A = 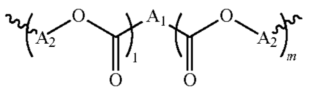

$A_1$ represents an alkyl radical, linear or branched, comprising from 2 to 40 carbon atoms, optionally from 2 to 12 carbon atoms, said radical optionally comprising one or more unsaturations, being optionally interrupted by at least one heteroatom selected from O, N and S, and being optionally substituted by at least one —OAlk substituent, Alk representing an alkyl group comprising from 1 to 10 carbon atoms;

$A_2$ represents an alkyl radical, linear or branched, comprising from 2 to 30 carbon atoms, optionally from 5 to 22 carbon atoms, said radical optionally comprising one or more unsaturations, and being optionally substituted by at least one —OAlk substituent, Alk representing an alkyl group comprising from 1 to 10 carbon atoms;

l and m represent, independently of each other, an integer from 1 to 20, optionally from 1 to 10, the sum l+m optionally being from 2 to 20;

n is an integer from 1 to 20, optionally from 2 to 8;

j is an integer from 1 to 10, optionally from 1 to 3;

X represents an alkyl radical, linear or branched, comprising from 2 to 60 carbon atoms, optionally 16 to 45 carbon atoms; and Y represents an alkyl radical, linear or branched, comprising from 3 to 35 carbon atoms, optionally from 6 to 18 carbon atoms, comprising the following steps:

step 1) Preparing preparing a polyamide precursor by functionalizing a diacid of formula (2) by a diamine of formula (3) to obtain a diamine polyamide of formula (4):

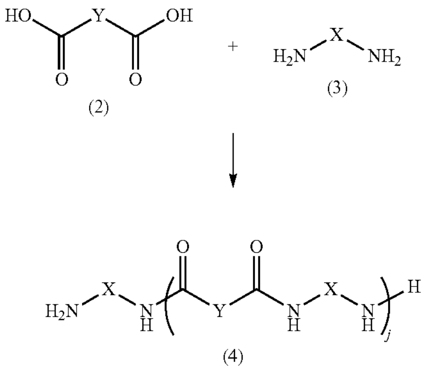

(2) (3) (4)

wherein j, X and Y are as defined above;

step 2) modifying a diacid polyester of formula (5)

(5)

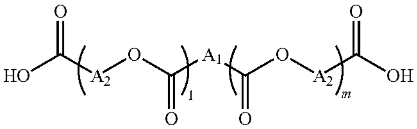

by adding the diamine polyamide of formula (4)

(4)

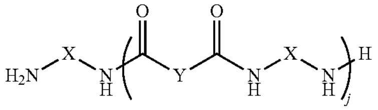

wherein $A_1$, $A_2$, X, Y, l, m, and j are as defined above, leading to the polyamide of formula (1) above.

7. The method according to claim 6, wherein the step 1) is implemented by mixing an equivalent of diacid of formula (2) and a quantity of diamine of formula (3) of between 1 and 4 equivalents, at a temperature of between 100° C. and 240° C., optionally between 130° C. and 150° C.

8. The method according to claim 6, wherein the step of modifying the diacid polyester of formula (5) by adding diamine polyamide of formula (4) leading to polyamide of formula (1) is implemented by adding 1 equivalent of diacid polyester of formula (5) to a quantity of diamine polyamide of formula (4) of between 0.2 and 1 equivalent, at a temperature of between 100 and 240° C., optionally between 130 and 150° C.

9. The method according to claim 6, further comprising terminating the chains of the polyamide compound of formula (1) by adding an alcohol termination compound of formula (6), leading to a polyamide compound of formula (7):

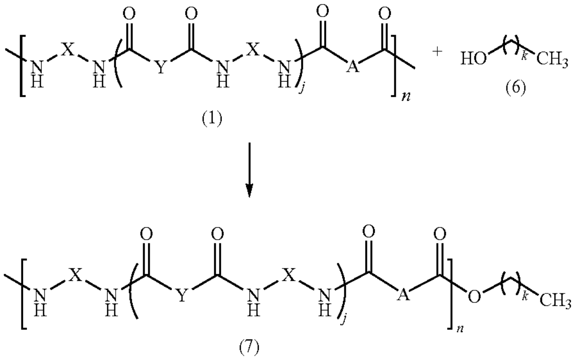

(1) (6) (7)

wherein:

A = 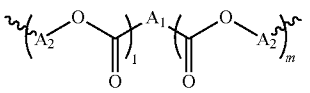

-X, Y, $A_1$, $A_2$, j, n, 1, and m are as defined in claim 6; and k is an integer from 2 to 60, optionally from 8 to 40.

10. A polyamide compound of formula (7)

(7)

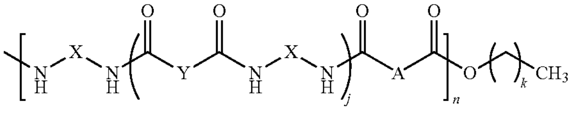

wherein:

A = 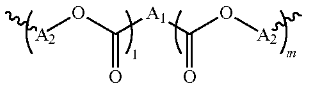

$A_1$ represents an alkyl radical, linear or branched, comprising from 2 to 40 carbon atoms, optionally from 2 to 12 carbon atoms, said radical optionally comprising one or more unsaturations, being optionally interrupted by at least one heteroatom selected from O, N and S, and being optionally substituted by at least one —OAlk substituent, Alk representing an alkyl group comprising from 1 to 10 carbon atoms;

$A_2$ represents an alkyl radical, linear or branched, comprising from 2 to 30 carbon atoms, optionally from 5 to 22 carbon atoms, said radical optionally comprising one or more unsaturations, and being optionally substituted by at least one —OAlk substituent, Alk representing an alkyl group comprising from 1 to 10 carbon atoms;

l and m represent, independently of each other, an integer from 1 to 20, optionally from 1 to 10, the sum l+m optionally being from 2 to 20;

n is an integer from 1 to 20, optionally from 1 to 8;

j is an integer from 1 to 10, optionally from 1 to 3;

k is an integer from 2 to 60, optionally from 8 to 40;

X represents an alkyl radical, linear or branched, comprising from 2 to 60 carbon atoms, optionally 16 to 45 carbon atoms, said radical optionally comprising one or more unsaturations; and Y represents an alkyl radical, linear or branched, comprising from 3 to 35 carbon atoms, optionally from 6 to 18 carbon atoms.

11. An oil-gelling agent comprising the polyamide of formula (1) according to claim 1.

12. A gel comprising the polyamide of formula (1) according to claim 1.

13. The gel according to claim 12, wherein the content by weight of the polyamide of formula (1) is between 0.5% and 10%, optionally from 3 to 8%.

14. A pharmaceutical or cosmetic composition comprising the polyamide of formula (1) according to claim 1.

15. A cosmetic composition comprising the gel according to claim 12, wherein the content by weight of the polyamide of formula (1) is between 0.5% and 10%, optionally from 3 to 8%.

16. An oil-gelling agent comprising the polyamide compound of formula (7) according to claim 10.

17. A gel comprising the polyamide compound of formula (7) according to claim 10.

18. The gel according to claim 17, wherein the content by weight of the polyamide of formula (7) is between 0.5% and 10%, optionally from 3 to 8%.

19. A pharmaceutical or cosmetic composition comprising the polyamide compound of formula (7) according to claim 10.

20. A cosmetic composition comprising the gel according to claim 17, wherein the content by weight of the polyamide of formula (7) is between 0.5% and 10%, optionally from 3 to 8%.

* * * * *